United States Patent [19]

Phuc

[11] Patent Number: 4,537,188
[45] Date of Patent: Aug. 27, 1985

[54] GAS JET DEVICE FOR USE IN RESPIRATORS

[75] Inventor: Tran N. Phuc, Ohmiya, Japan

[73] Assignee: Senki Medical Instrument Mfg. Co., Ltd., Tokyo, Japan

[21] Appl. No.: 460,652

[22] Filed: Jan. 24, 1983

[30] Foreign Application Priority Data

Jan. 26, 1982 [JP] Japan .................. 57-8906[U]

[51] Int. Cl.³ .............................................. A61M 16/00
[52] U.S. Cl. .............................. 128/200.21; 128/204.25
[58] Field of Search ................... 128/200.14, 200.18, 128/200.21, 203.17, 203.26, 203.27, 204.17, 204.25; 261/DIG. 65

[56] References Cited

U.S. PATENT DOCUMENTS

| | | | |
|---|---|---|---|
| 260,505 | 7/1882 | Studley | 128/200.14 |
| 2,826,454 | 3/1958 | Coanda | 128/200.18 |
| 2,869,188 | 1/1959 | Cameto | 128/200.21 |
| 3,647,143 | 3/1972 | Gauthier et al. | 128/200.14 |
| 4,165,740 | 8/1979 | Kurichev et al. | 128/200.14 |
| 4,425,914 | 1/1984 | Ray et al. | 128/200.14 |
| 4,427,004 | 1/1984 | Miller | 128/200.21 |

Primary Examiner—Henry J. Recla
Attorney, Agent, or Firm—Cushman, Darby & Cushman

[57] ABSTRACT

A gas jet device for use in respirators in which a respiratory gas supplied from a ventilator is injected in a jet state from the gas jet device into a patient circuit. The gas jet device includes a gas conduit for receiving the respiratory gas from the ventilator and jetting the respiratory gas from its forward end into the patient circuit, and a humidifying conduit for receiving water from a water source and supplying the water from its forward end to the respiratory gas, one of the humidifying conduit and the gas conduit surrounding at its forward end portion the forward end portion of the other.

3 Claims, 5 Drawing Figures

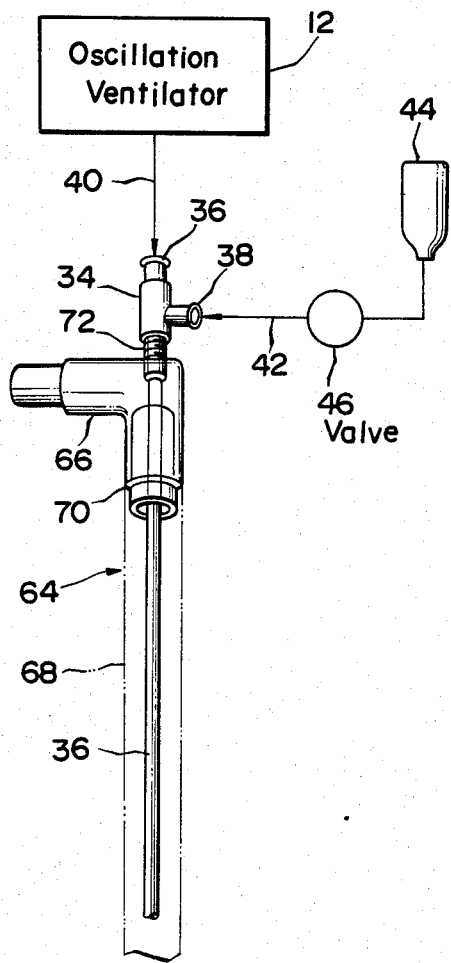

GAS JET DEVICE FOR USE IN RESPIRATORS

BACKGROUND OF THE INVENTION

The present invention relates to a gas jet device for use in respirators, and more particularly to a gas jet device to be connected to a patient circuit for supplying a humidified respiratory gas in a jet state to lungs of a patient through the patient circuit.

FIG. 1 shows a typical example of the conventional repirator, in which a gas source 10 supplies an oscillation ventilator 12 with a respiratory gas at a predetermined pressure level, the gas being oxygen gas or being composed of oxygen gas and air. The oscillation ventilator 12 provides a desired amount of the supplied gas at a predetermined frequency to a patient circuit 16 through a gas jet tube 14. The patient circuit 16 has a gas chamber 18 connected to the gas source 10 through a humidifier 17 for introducing the respiratory gas and an endotracheal tube 20 attached in a communicating relation to the gas chamber 18, the endotracheal tube being inserted from a mouth into a trachea of a patient. The gas chamber 18 is communicated to the atmosphere through a flexible pipe 23. The respiratory gas from the humidifier is passed to his lungs by the respiratory gas jetted from the oscillation ventilator 12. The tube portion 14A of the gas jet tube 14 is a thin tube of about 1 mm diameter, and is inserted into the gas chamber 18 so that the repiratory gas from the oscillation ventilator 12 may be jetted into that chamber. A humidifying tube 22 is inserted into the gas chamber 18 so that the forward end thereof is placed near that of the gas jet tube 14. The humidifying tube 22 is a thin tube of about 1 mm diameter, and is connected to a water source (not shown) for supplying moisture to the respiratory gas from the gas jet tube 14 by dripping water from its forward end.

However, the above-described respirator has a disadvantage in that sufficient moisture is not given to the respiratory gas from the gas jet tube 14 because water drops dripping from the humidifying tube 22 can be blown away or remain in the patient circuit 16, so that they cannot be mixed with the respiratory gas from the gas jet tube 14 in a sprayed state. The prior art respirator has a further disadvantage in that it is difficult to vary the feed of moisture to the respiratory gas supplied from the tube 14 in response to change in flow rate of that respiratory gas.

In order to avoid the above-described disadvantages of the prior art another humidifying structure shown in FIG. 2 has been proposed, in which the gas jet tube 14 is connected at its gas accumulating portion 14B to a water bottle 26 as a water source through a slender tube 28. A check valve 30 and a pump 32 are interposed between the accumulating portion 14B and the water bottle 26.

Although this humidifying structure is capable of spraying water into the respiratory gas, it also has the disadvantage that it is difficult to simultaneously adjust the flow rate of water pumped by the pump 32 in response to change in the feed of the respiratory gas. The above-described humidifying structure has a further disadvantage in that while the respiratory gas is jetted out from the gas jet tube 14, water is not supplied from the tube 28 and thus sufficient moisture is not continuously given to the respiratory gas. This is because when the respiratory gas passes through the tube 14, a high pressure is applied on the open end of the water tube 28 opening to the gas accumulating portion 14B of the gas jet tube 14, so that water in the tube 28 is pushed back toward the pump 32, which necessitates the provision of the check valve 30.

SUMMARY OF THE INVENTION

Accordingly, it is an object of the present invention to provide a gas jet device for use in respirators which appropriately adjusts the flow rate of water supplied to the gas jet conduit in response to and simultaneously with a change in the feed of a respiratory gas.

It is another object of the present invention to provide a gas jet tube for use in respirators which continuously provides an appropriate amount of moisture to the respiratory gas supplied.

It is a further object of the present invention to provide a gas jet device for use in respirators which makes it unnecessary to use a pump and a check valve for supplying moisture to the respiratory gas supplied, and is thus less complicated in structure than the prior art gas jet device.

In view of these and other objects in view, the present invention provides a gas jet device for use in respirators, including: a gas conduit for receiving a respiratory gas from a ventilator and jetting the resperatory gas from its forward end into the patient circuit; and a humidifying conduit for receiving water from a water source and supplying the water from its forward end to the respiratory gas, one of the humidifying conduit and the gas conduit surrounding at its free end portion a free end portion of the other.

BRIEF DESCRIPTION OF THE DRAWINGS

FIG. 5 is a diagrammatic illustration of the gas jet device in FIG. 3 when it is used.

DETAILED DESCRIPTION OF THE PREFERRED EMBODIMENT

Figure 3:
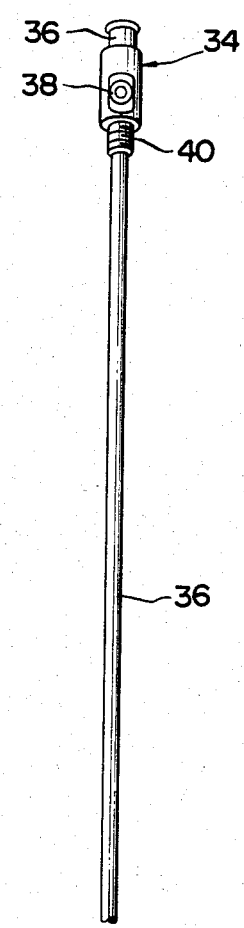
FIG. 3 is a side view of one embodiment of the present invention.
Figure 4:
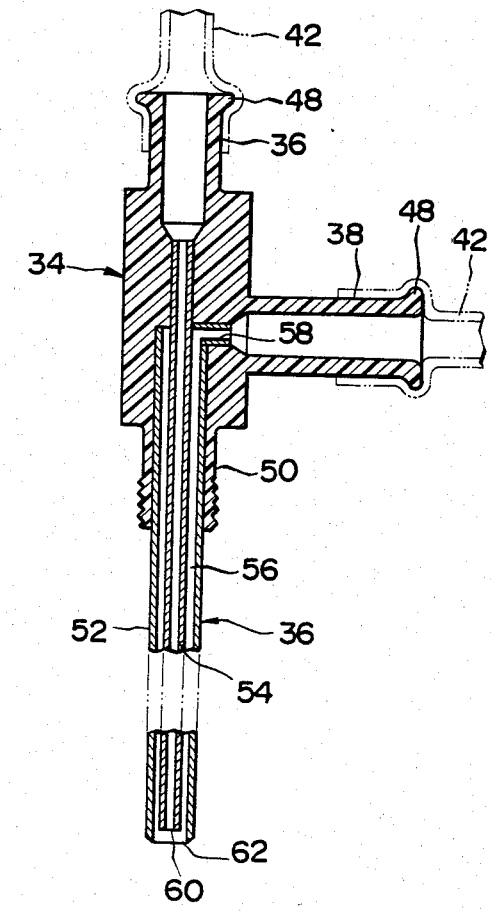
FIG. 4 is an enlarged vertical cross section of the gas jet device in FIG. 3.

Referring to FIGS. 3 to 5 the gas jet device according to the present invention includes a cylindrical connecting head 34 and an elongated thin double tube 36 fixedly attached to the connecting head 34, both members being of a corrosion-resisting material such as stainless steel. The connecting head 34 has a tube fitting portion 36 integrally formed with its top end to axially project from that head, and another tube fitting portion 38 integrally formed with its circumferential portion to laterally project from that head. These tube fitting portions 36 and 38 are of a hollow cylindrical shape, and are, as shown in FIG. 4 by a phantom line, tightly fitted around by connecting tubes 40 and 42. The tube 40 is connected to a oscillation ventilator as shown in FIG. 5 and tube 42 to a water source 44 through a valve 46. The valve 46 may be a regulating clamp when the tube 42 is a flexible synthtic resin tube. The tube fitting portions 36 and 38 are each provided at their outer open ends with a circumferential flange 48 partly cut out for preventing the connecting tubes 40 and 42 from slipping off from or loosely fitted around the tube fitting portions 36 and 38.

The connecting head 34 is further provided at its bottom end with a threaded portion 50 which axially projects from that bottom end. The double tube 36 coaxially passes through the threaded portion 50. The double tube 36 includes an outer tube 52 and an inner tube 54 which is coaxially inserted into and spacedly positioned within that outer tube so that humidifying conduit 56 is formed between the inner wall of the outer tube 52 and the outer wall of the inner tube 54. The inner tube 54 passes through the connecting head 34 to communicate to the tube fitting portion 36. The outer tube 52 is inserted into the connecting head 34 to its mid-portion and communicated to the tube fitting portion 38 through a connecting passage 58 formed in the connecting head 34, the connecting passage 58 meeting the rear end of the inner tube 54 with a right angle. The inner tube 54 is disposed so that its forward end 60 is positioned slightly inwardly of the forward end 62 of the outer tube 52. In the above-described structure of the connecting head 34, the tube fitting portion 36 and the inner tube 54 constitute a gas conduit for jetting out a respiratory gas from its forward end 60.

In the above-described embodiment, the cross-sectional area of the gas conduit at the inner tube 54 is within a range of about 0.75 mm$^2$ to about 2.90 mm$^2$, and on the other hand that of the humidifying conduit at the double pipe 36 is within a range of about 0.10 mm$^2$ to about 0.65 mm$^2$. The ratio of the cross-sectional area of the gas conduit to that of the humidifying conduit is 4:1 to 8:1 at the double pipe 36. This ratio is determined in view of the feed and flow rate of a respiratory gas to be supplied from the gas conduit and a suitable water content of the respiratory gas.

Figure 1:
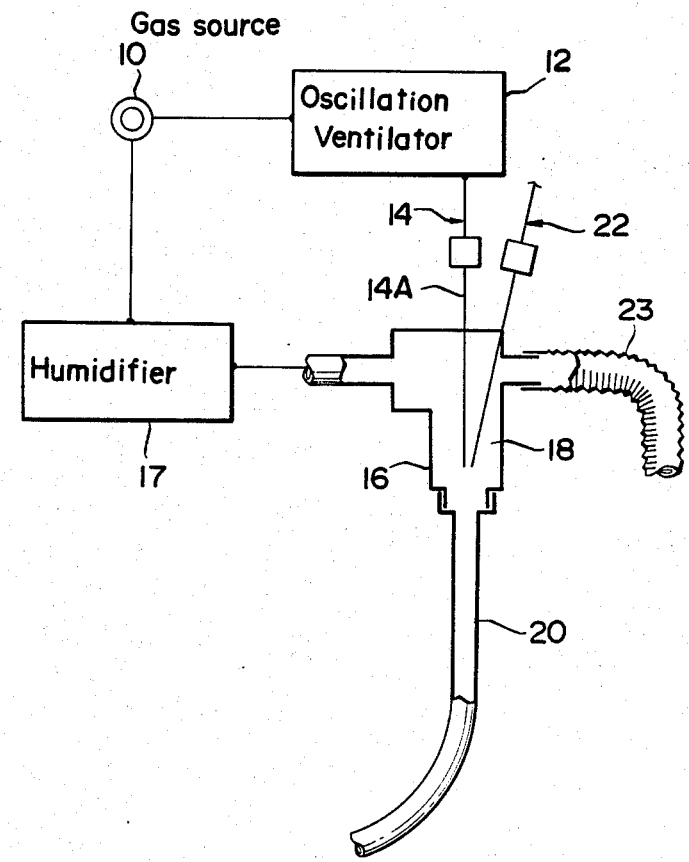
FIG. 1 is a diagrammatic illustration of a typical example of the conventional respirator.
Figure 2:
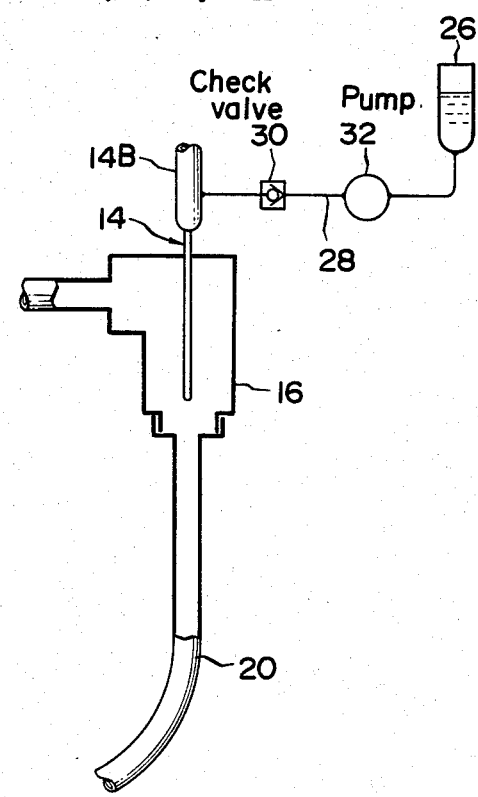
FIG. 2 is a diagrammatic illustration of another typical example of the conventional respirator.

When used, the gas jet device having the above-described structure is as shown in FIG. 5 attached to a patient circuit 64 which has an L-shaped tube connector 66 of a transparent material. The tube connector 66 may be of a plastic resin such as polycarbonate, acrylic resin, and the like. The tube connector 66 further has an endotracheal tube 68 (shown by a phantom line) tightly fitted around one end 70 of that L-shaped connector 66, the endotracheal tube 68 being of substantially the same structure as that in FIG. 1. More specifically, the double tube 36 of the gas jet device is inserted into a boss 72 with a threaded inner wall integrally formed with the L-shaped connector 66, and then the threaded portion 50 of the connecting head 34 is threadedly engaged with the threaded inner wall of the boss 72, so that the free end of the double tube 36 passes through the one end 70 of the L-shaped connector 66 into the endotracheal tube 68. In operation, the oscillatory ventilator 12 is actuated to periodically supply a respiratory gas through the connecting tube 40 to the connecting head 34. The periodically supplied respiratory gas is passed through the gas conduit of the inner tube 54 and then ejected from the forward end 60 of that inner tube into the endotracheal tube 68, in which event water in the humidifying conduit 56 which is supplied from the water source 44 through the conduit is aspirated from the forward end 62 of the outer pipe 52 into a jet of that respiratory gas from the inner pipe 54 so that it is mixed with the respiratory gas in a sprayed state.

In the above embodiment it is to be noted that the forward end 60 of the inner pipe 54 is inwardly spaced away from the forward end 62 of the outer pipe 52. Thus, water is supplied slightly ahead of the forward end 60 of the inner pipe 54, so that water is smoothly carried away by the jet of the respiratory gas. Accordingly, the greater the flow rate or feed of the respiratory gas increases, the larger the mount of water carried away becomes. The moisture content of the respiratory gas is automatically regulated according to the feed of the respiratory gas. The water sprayed into and mixed with the respiratory gas turns into vapor before it reaches lungs of a patient through the endotracheal tube 68, and thus the respiratory gas with a suitable moisture is provided. When the respiratory gas is not injected from the forward end 60 of the inner pipe 54, water is not dripped from the forward end 62 of the outer pipe 52 due to its surface tension since the cross-sectional area of the humidifying conduit is sufficiently small. Therefore, this gas jet device does not adversely affect a patient by allowing water drops to fall into the patient circuit or introducing them through that patient circuit into his lungs during the stop of the gas supply from the forward end 60 of the inner tube 54 which periodically occurs.

In a modified form of the gas jet device in FIGS. 3 to 5, water may be passed through the inner tube while a respiratory gas may be passed through the conduit 56 between the outer tube 52 and the inner tube 54.

While the invention has been disclosed in specific detail for purposes of clarity and complete disclosure, the appended claims are intended to include within their meaning all modifications and changes that come within the true scope of the invention.

What is claimed is:

1. In a humidified respiratory gas jet device for injecting in a humidified state into a patient circuit a respiratory gas supplied from an oscillation ventilator, the improvement which comprises:

an oscillation ventilator constructed and arranged for providing an oscillating supply of ventilating gas; and a gas jet device operatively connected to said oscillation ventilator, said gas jet device including:

(a) a connecting member having:

a first inlet adapted to be connected to a water source to receive water, a second inlet connected to said oscillation ventilator to receive an oscillating stream of respiratory gas therefrom.

a first water passage formed in said connecting member, opening at one end thereof, said first water passage being substantially straight, a second water passage connecting another end of the first water passage to said first inlet, and a gas passage formed in said connecting member to communicate at one end thereof to the second inlet and at another end to the first water passage, said gas passage being substantially straight and in alignment with said first water passage;

(b) a first straight pipe connected at one end to said first water passage to receive water therefrom;

(c) a second straight pipe connected at one end to said gas passage, said second straight pipe and said gas passage being arranged to form a straight gas conduit for transporting the respiratory gas and having another end portion coaxially fitted into said first straight pipe to form an annular humidifying conduit between an inner wall of the first pipe and an outer wall of the second pipe for conducting the water from the water source, said other end of said second straight pipe being axially inwardly spaced from said other end of said first straight pipe;

said one end of said second pipe being sealingly fitted into said gas passage to pass through the gas passage to thereby directly communicate with said second inlet; and said one end of said first pipe being securely fitted into said first water passage; and (d) the ratio of the cross-sectional area of said straight gas conduit to the cross-sectional area of said humidifying conduit being 4:1 to 8:1 at said other end of said second pipe, the cross-sectional area of said straight gas conduit at said other end of the second pipe being within the range of about 0.75 mm$^2$ to about 2.90 mm$^2$.

2. A device as recited in claim 1, wherein:

said connecting member further includes means, integrally formed therewith, for detachably attaching said connecting member to a patient circuit, said first pipe and said second pipe passing through said attaching means.

3. A device as recited in claim 2, wherein:

said attaching means comprises a threaded portion, integrally formed with said connecting member, for threadedly engaging with the patient circuit to communicate the gas conduit and said humidifying conduit to the patient circuit.

* * * * *

UNITED STATES PATENT AND TRADEMARK OFFICE
CERTIFICATE OF CORRECTION

PATENT NO.   :   4,537,188
DATED        :   August 27, 1985
INVENTOR(S)  :   Tran N. PHUC It is certified that error appears in the above-identified patent and that said Letters Patent is hereby corrected as shown below:

On the Title Page, the Assignee is incorrect. Should read:

--SENKO MEDICAL INSTRUMENT MFG. CO., LTD.--

Signed and Sealed this

Twenty-fourth Day of December 1985

[SEAL]

Attest:

DONALD J. QUIGG

Attesting Officer

Commissioner of Patents and Trademarks